US012331322B2

(12) United States Patent
Nojima et al.

(10) Patent No.: US 12,331,322 B2
(45) Date of Patent: *Jun. 17, 2025

(54) AGENT FOR ACCELERATING GROWTH OF PLURIPOTENT STEM CELLS

(71) Applicant: Oriental Yeast Co., Ltd., Tokyo (JP)

(72) Inventors: Jun Nojima, Tokyo (JP); Hidenori Matsuo, Nagahama (JP); Yuriko Furuya, Nagahama (JP); Hisataka Yasuda, Nagahama (JP)

(73) Assignee: ORIENTAL YEAST CO., LTD., Tokyo (JP)

( * ) Notice: Subject to any disclaimer, the term of this patent is extended or adjusted under 35 U.S.C. 154(b) by 127 days.

This patent is subject to a terminal disclaimer.

(21) Appl. No.: 18/064,441

(22) Filed: Dec. 12, 2022

(65) Prior Publication Data

US 2023/0115507 A1 Apr. 13, 2023

Related U.S. Application Data

(63) Continuation of application No. 16/481,760, filed as application No. PCT/JP2018/003172 on Jan. 31, 2018, now Pat. No. 11,634,690.

(30) Foreign Application Priority Data

Jan. 31, 2017 (JP) ................... 2017-015313

(51) Int. Cl.
C12N 5/074 (2010.01)
C12N 5/0775 (2010.01)
(52) U.S. Cl.
CPC ......... *C12N 5/0696* (2013.01); *C12N 5/0662* (2013.01); *C12N 2501/999* (2013.01)
(58) Field of Classification Search
CPC ..... C12N 5/0696; C12N 5/0662; C12N 5/071
See application file for complete search history.

(56) References Cited

U.S. PATENT DOCUMENTS

| 7,737,158 B2 | 6/2010 | Imai et al. |
| 2013/0011921 A1 | 1/2013 | Hishida et al. |
| 2013/0059384 A1 | 3/2013 | Tilly et al. |
| 2015/0072416 A1 | 3/2015 | Cho et al. |
| 2016/0022712 A1 | 1/2016 | Mai et al. |

FOREIGN PATENT DOCUMENTS

| CN | 104367587 A | 2/2015 |
| JP | 2014-520526 | 8/2014 |
| JP | 2015-507921 | 3/2015 |
| WO | 2011/102333 | 8/2011 |
| WO | 2013/002880 | 1/2013 |
| WO | 2013/121426 | 8/2013 |
| WO | 2014/146044 | 9/2014 |
| WO | 2016/038011 | 3/2016 |

OTHER PUBLICATIONS

Office Action issued for Chinese Patent Application No. 201880019706.9, Nov. 9, 2022, 17 pages including English translation.
Office Action issued for U.S. Appl. No. 16/481,760 on Mar. 23, 2022, 9 pages.
Final Rejectoin issued for U.S. Appl. No. 16/481,760 on Sep. 12, 2022, 9 pages.
Son, et al., Stem Cells, 2013, vol. 31, p. 1121-1135.
Zhao et al., Stroke, 2015, vol. 46, No. 7, p. 1966-1974.
Wiley et al., The EMBO Journal, vol. 33, No. 12, p. 1289-1291, 2014.
International Search Report of PCT/JP2018/003172, mailed on May 1, 2018, 4 pages, with English translation.
The extended European Search Report issued for European Patent Application No. 18748681.6. Jun. 8, 2020, 7 pages.
Parsons (2011, Jove, 57:e327 4, pp. 1-6).
Li, Journal of Bone and Mineral Research, vol. 26, No. 11, Nov. 2011, pp. 2656-2664.

*Primary Examiner* — Valarie E Bertoglio
(74) *Attorney, Agent, or Firm* — HSML P.C.

(57) ABSTRACT

An object of the present invention is to provide a material capable of further accelerating growth of pluripotent stem cells, such as pluripotent stem cells, without impairing pluripotency thereof. In other words, the invention is an agent for accelerating growth of pluripotent stem cells, containing a β-nicotinamide mononucleotide or a pharmaceutically acceptable salt thereof, and a solvate thereof as an active ingredient; and is a method for culturing pluripotent stem cells, including culturing pluripotent stem cells in a culture medium that contains a β-nicotinamide mononucleotide or a pharmaceutically acceptable salt thereof, and a solvate thereof.

7 Claims, 6 Drawing Sheets

AGENT FOR ACCELERATING GROWTH OF PLURIPOTENT STEM CELLS

This application is a continuation application of U.S. patent application Ser. No. 16/481,760, which has been issued as U.S. Pat. No. 11,634,690, which is a national stage entry of PCT/JP2018/003172.

TECHNICAL FIELD

The present invention relates to a material capable of further accelerating growth of pluripotent stem cells without impairing pluripotent differentiation potential thereof, and a method for culturing pluripotent stem cells in which the material is used.

Priority is claimed on Japanese Patent Application No. 2017-015313, filed Jan. 31, 2017, the content of which is incorporated herein by reference.

BACKGROUND

Pluripotent stem cells are undifferentiated cells having a self-renewal ability and are cells capable of pluripotent differentiating into various cells. In recent years, regenerative medicine in which pluripotent stem cells and cells differentiation-induced from the pluripotent stem cells are transplanted into damaged tissues of a patient to regenerate their functions has been actively studied. In regenerative medicine, because large amounts of pluripotent stem cells and differentiated cells thereof are required to be prepared, development of methods for efficiently growing pluripotent stem cells is also active. In particular, pluripotent stem cells lose their pluripotency during culture in many cases, and thus a method for growing pluripotent stem cells while maintaining their pluripotency has been required.

As a method for culturing pluripotent stem cells, for example, it is reported that mesenchymal stem cells efficiently grow by culturing them in a medium containing nicotinamide (NAM) and a fibroblast growth factor 4 (FGF4) (refer to, for example, Patent Literature 1). In addition, it is also reported that NAM resolves loss of pluripotency of pluripotent stem cells and impairment of reprogramming (refer to, for example, Non-Patent Literature 1). In addition, it is reported that, when induced pluripotent stem cells (iPS cells) are cultured in the presence of NAM, NAM suppresses the function of sirtuins or PARP, and thereby iPS cells of which gene expression patterns are similar to those of embryonic stem cells (ES cells) can be efficiently manufactured (refer to, for example, Patent Literature 2).

Meanwhile, nicotinamide mononucleotide (NMN) is a biosynthetic intermediate metabolite of the coenzyme $NAD^+$. In recent years, it has been reported that NMN exhibits an effect of ameliorating insulin secretory ability in senescent mice, exhibits an effect of drastically ameliorating insulin sensitivity and secretion in a mouse model with type 2 diabetes caused by high-fat diet and aging (refer to, for example, Patent Literature 3), and exhibits an effect of significantly enhancing a mitochondrial function of aged muscle. In addition, it has been reported that administration of NMN is useful for ameliorating or preventing symptoms of various age-related diseases such as obesity, elevated blood triglyceride and low-density lipoprotein cholesterol levels, decreased insulin sensitivity, decreased memory ability, and ocular function deterioration such as macular degeneration (refer to, for example, Patent Literature 4).

CITATION LIST

Patent Literature

Patent Literature 1

Published Japanese Translation No. 2015-507921 of the PCT International Publication Patent Literature 2

PCT International Publication No. WO2011/102333

Patent Literature 3

U.S. Pat. No. 7,737,158

Patent Literature 4

PCT International Publication No. WO2014/146044

Non-Patent Literature

Non-Patent Literature 1

Son, et al., STEM CELLS, 2013, vol. 31, p. 1121-1135.

SUMMARY OF INVENTION

Technical Problem

An object of the present invention is to provide a material capable of further accelerating growth of pluripotent stem cells without impairing pluripotency thereof, and a method for culturing pluripotent stem cells in which the material is used.

Solution to Problem

As a result of intensive studies to achieve the above-described object, the inventors of the present invention have found that growth of pluripotent stem cells is accelerated in the presence of β-nicotinamide mononucleotide (β-NMN) and pluripotency thereof is not impaired, and therefore have completed the invention.

In other words, the invention provides the following agent for accelerating growth of pluripotent stem cells, a method for culturing pluripotent stem cells, and a method for accelerating growth of pluripotent stem cells.

[1] An agent for accelerating growth of pluripotent stem cells, containing, as an active ingredient: a β-nicotinamide mononucleotide or pharmaceutically acceptable salt thereof; and a solvate thereof.

[2] The agent according to [1], which is added at 0.01 to 5 mM into a culture medium for pluripotent stem cells in terms of β-nicotinamide mononucleotide.

[3] The agent according to [1] or [2], which is used for accelerating growth of one or more kinds of pluripotent stem cells selected from the group consisting of embryonic stem cells, induced pluripotent stem cells, and mesenchymal stem cells.

[4] A method for culturing pluripotent stem cells, including culturing pluripotent stem cells in a culture medium that contains a β-nicotinamide mononucleotide or a pharmaceutically acceptable salt thereof, and a solvate thereof.

[5] The method according to [4], in which a concentration of the β-nicotinamide mononucleotide of the culture medium is 0.01 to 5 mM.

[6] The method according to [4] or [5], in which the pluripotent stem cells are one or more kinds selected from the group consisting of embryonic stem cells, induced pluripotent stem cells, and mesenchymal stem cells.

[7] A method for accelerating growth of pluripotent stem cells, including culturing pluripotent stem cells in a culture medium that contains a β-nicotinamide mononucleotide or a pharmaceutically acceptable salt thereof, and a solvate thereof.

Advantageous Effects of Invention

The agent for accelerating growth of pluripotent stem cells according to the present invention acts on pluripotent stem cells such as induced pluripotent stem cells (iPS cells), embryonic stem cells (ES cells) and the like thereby can accelerate growth thereof while maintaining their pluripotency. For this reason, by incorporating the agent for accelerating growth of pluripotent stem cells in a culture medium, larger amounts of pluripotent stem cells can be efficiently prepared.

DESCRIPTION OF EMBODIMENTS

Figure 1:
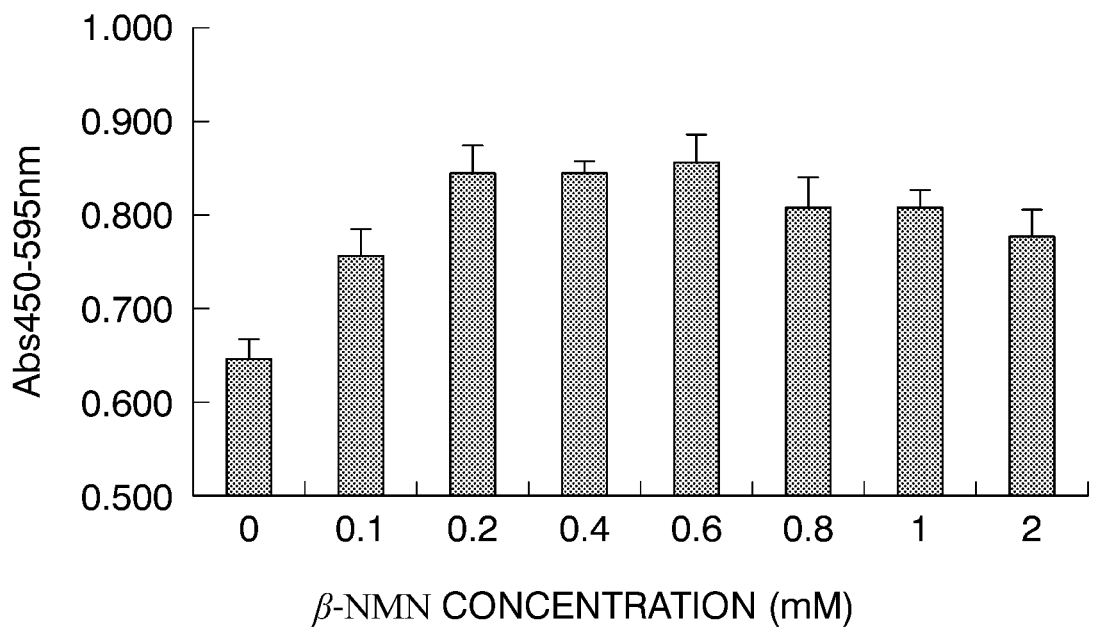
FIG. 1 is a graph showing results of measuring absorbance values at 450 nm (ref. 595 nm) for each β-NMN concentration of a culture medium with WST assay on wells in which iPS cells (201B7) are cultured in the culture medium to which β-NMN is added in Example 1.

In the present invention and the specification of the present application, pluripotent stem cells are undifferentiated cells which have self-renewal ability and pluripotency (an ability to differentiate into various cell types), and are preferably pluripotent stein cells that can differentiate into any of ectodermal, mesodermal, and endodermal cells. Examples of pluripotent stem cells include ES cells, iPS cells, mesenchymal stem cells, and the like.

An agent for accelerating growth of pluripotent stem cells according to the present invention (hereinafter referred to as the "growth-accelerating agent of the invention" in some cases) contains NMN (chemical formula: $C_{11}H_{15}N_2O_8P$) as an active ingredient, and is added to a culture medium when culturing pluripotent stem cells. By culturing pluripotent stem cells in the presence of NMN, pluripotent stem cells can grow more efficiently while maintaining pluripotency thereof.

Regarding NMN, there are two types of α and β as optical isomers, but NMN, which is used as the active ingredient of the growth-accelerating agent of the present invention, is β-NMN (CAS number: 1094-61-7). A structure of β-NMN is shown below.

[Chem. 1]

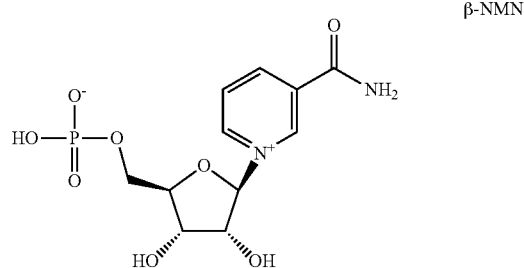

β-NMN

β-NMN may be prepared by any method. For example, β-NMN obtained by purifying β-NMN artificially synthesized by a chemical synthesis method, an enzymatic method, a fermentation method, or the like can be used as the active ingredient. In addition, because β-NMN is a component widely present in a living body, β-NMN obtained by extraction and purification from natural raw materials such as animals, plants, and microorganisms can also be used as the active ingredient. Furthermore, commercially available purified β-NMN may be used.

As a chemical synthesis method for synthesizing β-NMN, for example, β-NMN can be produced by reacting NAM with L-ribose tetraacetate, and phosphorylating the obtained nicotinamide mononucleotide. In addition, as an enzymatic method, for example, β-NMN can be produced from NAM and 5'-phosphoribosyl-1'-pyrophosphate (PRPP) by nicotinamide phosphoribosyltransferase (NAMPT). As a fermentation method, for example, β-NMN can be produced from NAM using a metabolic system of a microorganism expressing NAMPT.

The active ingredient of the growth-accelerating agent of the invention may be pharmaceutically acceptable salts of β-NMN. The pharmaceutically acceptable salt of β-NMN may be an inorganic acid salt or an organic acid salt having a basic site such as an amine. Examples of acids constituting such acid salts include acetic acid, benzenesulfonic acid, benzoic acid, camphorsulfonic acid, citric acid, ethenesulfonic acid, fumaric acid, gluconic acid, glutamic acid, hydrobromic acid, hydrochloric acid, isethionone acids, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid, p-toluenesulfonic acid, and the like. In addition, the pharmaceutically acceptable salt of β-NMN may be an alkali salt or an organic salt having an acidic site such as a carboxylic acid. Examples of bases constituting such acid salts include bases which are alkali metal salts or alkaline earth metal salts and which are induced from bases such as sodium hydride, potassium hydroxide, calcium hydroxide, aluminum hydroxide, lithium hydroxide, magnesium hydroxide, zinc hydroxide, ammonia, trimethyl ammonia, triethyl ammonia, ethylene diamine, lysine, arginine, ornithine, choline, N,N'-dibenzyl ethylenediamine, chloroprocaine, procaine, diethanolamine, N-benzylphenethylamine, diethylamine, piperazine, tris(hydroxymethyl)-aminomethane, and tetramethyl ammonium hydroxide.

The active ingredient of the growth-accelerating agent of the invention may be a solvate of free β-NMN or pharmaceutically acceptable salts thereof. Examples of solvents that form the above-mentioned solvate include water, ethanol, and the like.

The growth-accelerating agent of the invention may contain other active ingredients in addition to β-NMN. It is possible to appropriately select the other active ingredients from, for example, a component known to enhance survival efficiency or growth efficiency of pluripotent stein cells, or a component known to have an effect of maintaining an undifferentiated state of pluripotent stem cells; and to use them. Examples of components that enhance survival efficiency of pluripotent stem cells include Rho kinase (ROCK) inhibitors. In addition, examples of components for maintaining an undifferentiated state of pluripotent stem cells include FGF-2 and TGFβ superfamily. TGFβ superfamily includes TGF-β1, activin, NODAL, and the like. The other active ingredients to be used in combination with β-NMN may be only one kind or a combination of two or more kinds thereof.

By incorporating the growth-accelerating agent of the invention in a culture medium when pluripotent stem cells are cultured, growth of the pluripotent stem cells can be accelerated while maintaining differentiation potential thereof. An amount of the agent of the invention to be added to a culture medium is not particularly limited as long as the amount is an amount in which a concentration is sufficient to accelerate growth of pluripotent stem cells as compared to a case of culture in a culture medium not containing the agent, and the amount can be appropriately adjusted in consideration of the type of pluripotent stem cells, the balance with other components of the culture medium, and the like. In a case where a concentration of β-NMN in the culture medium is too low, a growth-accelerating effect on pluripotent stem cells may be weak, and in a case where β-NMN is excessively contained, growth may be suppressed conversely. A content of the growth-accelerating agent of the present invention in a culture medium is preferably a content in which a β-NMN concentration is 0.01 to 5 mM, more preferably 0.05 to 2 mM, even more preferably 0.1 to 1 mM. When a β-NMN concentration is within the above range, growth of pluripotent stem cells can be sufficiently accelerated while maintaining pluripotency thereof. A growth-accelerating effect of β-NMN is superior to other NAM-related substances such as NAM, nicotinic acid, and nicotinamide riboside.

Culturing of pluripotent stem cells in the presence of the growth-accelerating agent of the invention can be performed by general methods except that a culture medium contains the agent of the invention. For example, as a culture medium, it is possible to use a medium generally used for maintenance or growth of pluripotent stem cells, and a medium used for culture of animal cells. In addition, it is possible to use various commercially available culture media for pluripotent stem cells. In the present invention, examples of media that contain the agent of the invention and are used for culture of pluripotent stem cells include Eagle's Minimal Essential Medium (MEM), Dulbecco's modified Eagle's medium (DMEM), Minimum Essential Medium Eagle-α (αMEM), Iscove's Modified Dulbecco's Medium (IMDM), F-12 medium, F-10 medium, DMEM/F12 medium, RPMI-1640 medium, mesenchymal cell basal medium (MSCBM), E8 (Essential 8) medium, TeSR-E8 medium, mTeSR1 medium, and the like. If necessary, amino acids, inorganic salts, vitamins, antibiotics, and the like may be added to these media.

In these culture media, a component known to enhance survival efficiency or growth efficiency of pluripotent stem cells, or a component known to have an effect of maintaining an undifferentiated state of pluripotent stem cells, and the like may be appropriately contained in addition to the growth-accelerating agent of the invention. As these components, components described above can be used.

In addition, culture conditions can be set as general culture conditions for culturing animal cells, and may be suitably modified as necessary. For example, culture can be performed at a culture temperature of 30 to 40° C., a $CO_2$ concentration of 1 to 10% by volume, and an $O_2$ concentration of 0.1 to 25% by volume.

As pluripotent stem cells in which growth is accelerated by the growth-accelerating agent of the invention, pluripotent stem cells derived from mammal are preferable; pluripotent stem cells derived from human are more preferable; and pluripotent stein cells derived from human are particularly preferable. As pluripotent stem cells in which growth is accelerated by the agent of the invention, ES cells, iPS cells, or mesenchymal stem cells are preferable; ES cells, iPS cells, or mesenchymal stem cells which are derived from human are more preferable; and ES cells or iPS cells which are derived from human are even more preferable.

EXAMPLES

Next, the present invention will be described in more detail by showing examples, but the invention is not limited to the following examples.

Example 1 iPS cells were cultured in a culture medium containing β-NMN, and an effect of β-NMN on growth was examined. As iPS cells, 201B7 line which is human iPS cells was used. For iPS cells, an E8 medium (LTC) containing 19.4 mg/L of insulin, 10.7 mg/L of transferrin, 100 μg/L of bFGF, 2 μg/L of TGFβ, 14 μg/L of sodium selenite, 64 mg/L of ascorbic acid, and 543 mg/L of $NaHCO_3$ in DMEM/F12 was used as the basal medium.

First, iPS cells cultured in the basal medium were separated from a culture vessel by a cell-peeling solution and recovered. The recovered cells were counted and seeded in each well of a Matrigel-coated 96-well plate at 1000 to 2000 cells/well. At this time, a ROCK inhibitor was added to each well. The 96-well plate was cultured at 37° C. for 1 day to allow the cells to adhere, and then the medium containing the ROCK inhibitor was removed from each well, the medium was replaced with a medium obtained by adding, to the basal medium, β-NMN (Oriental Yeast Co., Ltd.) so that a final concentration became 0 to 2 mM, and culturing was performed for 3 to 4 days.

Thereafter, a growth ability of cells surviving in each well was measured by water-soluble tetrazolium salts (WST) assay. Specifically, after adding WST-1 (manufactured by Nacalai Tesque) to each well and incubating at 37° C. for 1 to 4 hours, absorbance values at 450 nm (ref. 595 nm) were measured using a microplate reader (manufactured by BMG LABTECH). The term "absorbance value (450 to 595 nm)" is an absorbance value at 450 nm using an absorbance value at 595 nm as a reference value, and is specifically a value obtained by subtracting an absorbance value at 595 nm from an absorbance value at 450 nm.

The results of the absorbance values at 450 nm (ref. 595 nm) for each β-NMN concentration of the medium are shown in FIG. 1. The absorbance values at 450 nm (ref. 595 nm) of the cells cultured in the medium containing 0.1 mM or more of β-NMN was greater than that of the cells cultured in the β-NMN-free medium (β-NMN: 0 mM), and therefore it was found that growth of iPS cells was accelerated in the presence of β-NMN. In particular, when a concentration of β-NMN was 0.1 to 0.2 mM, the absorbance value increased in a concentration-dependent manner; when a concentration of β-NMN was 0.2 to 0.6 mM, the absorbance value was the same; and when a concentration of β-NMN was 0.8 mM or more, the absorbance value tended to slightly decrease in a β-NMN concentration-dependent manner.

Example 2 iPS cells were cultured in a culture medium containing β-NMN or NAM, and the effects of β-NMN and NAM on growth were compared. As iPS cells, 201B7 line was used.

Specifically, iPS cells were cultured and the WST assay was performed in the same manner as in Example 1 except that the medium added after removing the medium containing the ROCK inhibitor was changed to a culture medium to which β-NMN was added so that a final concentration became 0, 0.2, or 0.4 mM, or a culture medium to which NAM was added so that a final concentration became 0, 0.2, or 0.4 mM.

Figure 2:
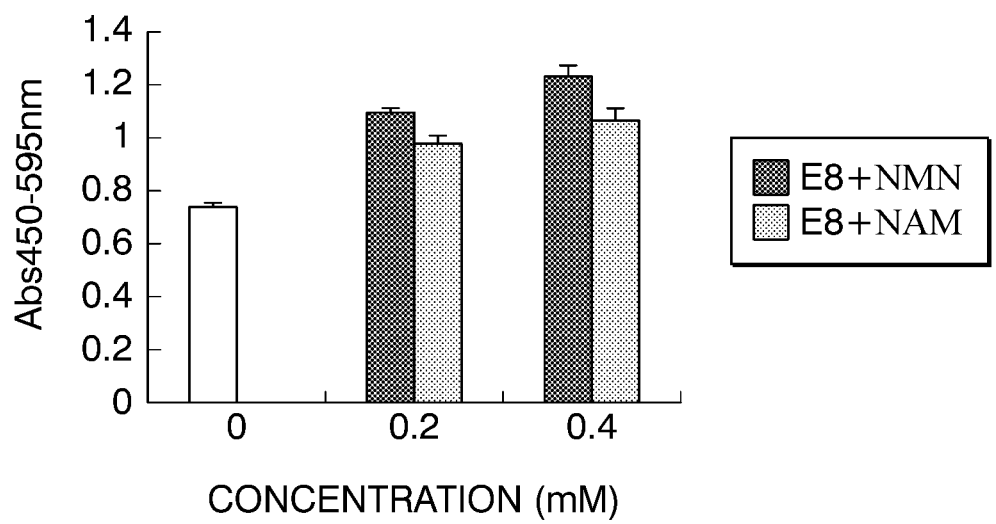
FIG. 2 is a graph showing results of measuring absorbance values at 450 nm (ref. 595 nm) for each of β-NMN concentration or NAM concentration of a culture medium with WST assay on wells in which iPS cells (201B7) are cultured in the culture medium to which β-NMN or NAM is added in Example 2.

The results of the absorbance values at 450 nm (ref. 595 nm) for each culture medium are shown in FIG. 2. In FIG. 2, "E8+NMN" is the results of the medium to which each concentration of β-NMN was added, and "E8+NAM" is the results of the medium to which each concentration of NAM was added. As shown in FIG. 2, both the cells cultured in the medium to which β-NMN was added and the cells cultured in the medium to which NAM was added have higher absorbance values than cells cultured in the basal medium, which means that both β-NMN and NAM had a growth-accelerating effect on iPS cells. In both the case in which a final concentration of the medium was 0.2 mM and the case in which a final concentration of the medium was 0.4 mM, the absorbance value of the cells cultured in the β-NMN-added medium was significantly higher than that of the cells cultured in the NAM-added medium, and therefore β-NMN was confirmed to have a higher growth-accelerating effect than NAM.

Example 3 iPS cells were cultured in culture medium containing β-NMN or NAM, and the effects of β-NMN and NAM on growth were compared. As iPS cells, 253G1 line was used.

Specifically, iPS cells were cultured and WST assay was performed in the same manner as in Example 1 except that 253G1 line was used instead of 201B7 line.

Figure 3:
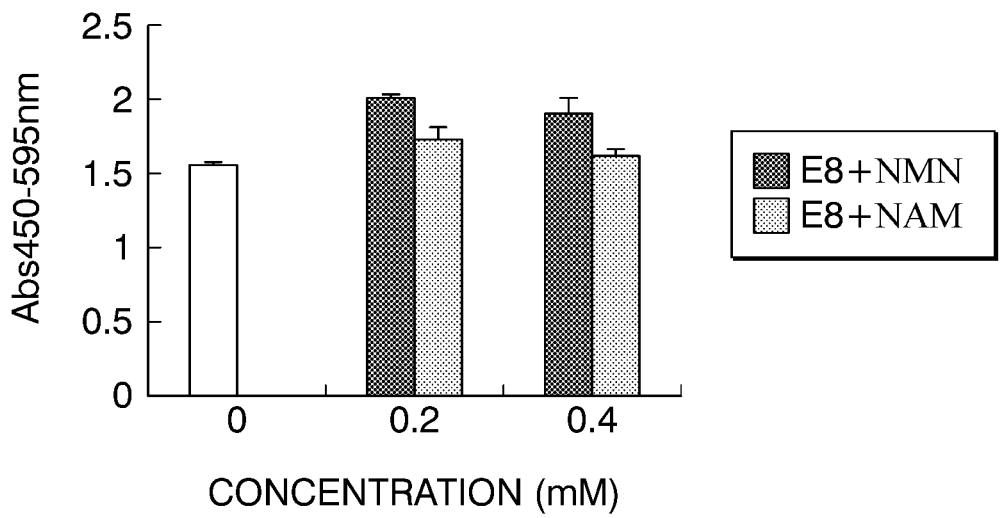
FIG. 3 is a graph showing results of measuring absorbance values at 450 nm (ref. 595 nm) for each of β-NMN concentration or NAM concentration of a culture medium with WST assay on wells in which iPS cells (253G1) are cultured in the culture medium to which β-NMN or NAM is added in Example 3.

The results of the absorbance values at 450 nm (ref. 595 nm) for each culture medium are shown in FIG. 3. In FIG. 3, "E8+NMN" is the results of the medium to which each concentration of β-NMN was added, and "E8+NAM" is the results of the medium to which each concentration of NAM was added. 0 mM on the graph is the result with the E8 medium. As shown in FIG. 3, the cells cultured in the medium to which β-NMN was added have a higher absorbance value than that of the cell cultured in the basal medium, and β-NMN also has a growth-accelerating effect on the 253G1 line. On the other hand, the cells cultured in the medium to which NAM was added have a slightly higher absorbance value than that of the cells cultured in the basal medium, but no clear growth-accelerating effect as in the case of β-NMN could be confirmed. Therefore, it was found that a growth-accelerating effect of NAM could not be obtained sufficiently depending on lines. In addition, as in the results of Example 2, in both the case in which a final concentration of the medium was 0.2 mM and the case in which a final concentration of the medium was 0.4 mM, the absorbance value of the cells cultured in the β-NMN-added medium was significantly higher than that of the cells cultured in the NAM-added medium, and therefore β-NMN was confirmed to also have a higher growth-accelerating effect on 253G1 line than NAM. Based on these results, β-NMN clearly has a significantly superior growth-accelerating effect on various iPS cells than NAM.

Example 4 iPS cells were cultured in a culture medium containing β-NMN, and the effects of β-NMN on differentiation potential and growth were examined. As iPS cells, a 201B7 line was used. The differentiation potential was examined using the enzyme activity of alkaline phosphatase, which is an undifferentiated marker, as an indicator.

<Effect on Growth>

The iPS cells cultured in the basal medium used in Example 1 were separated from a culture vessel by a cell-peeling solution and recovered. The recovered cells were counted and seeded in each well of a Matrigel-coated 96-well plate at 1000 to 2000 cells/well. At this time, a ROCK inhibitor and β-NMN having a final concentration of 0 to 1 mM were added to each well. The cells in 96-well plate was cultured at 37° C. for 1 day to allow the cells to adhere, and then the medium containing the ROCK inhibitor was removed from each well, the medium was replaced with a culture medium obtained by adding, to the basal medium, β-NMN so that a final concentration became 0 to 1 mM, and culturing was performed for 3 to 4 days.

Figure 4:
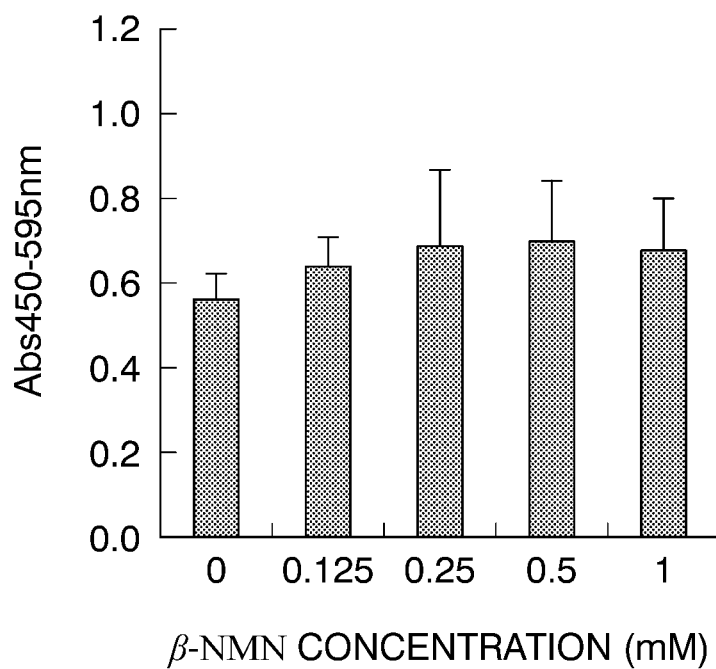
FIG. 4 is a graph showing results of measuring absorbance values at 450 nm (ref. 595 nm) for each β-NMN concentration of a culture medium with WST assay on wells in which iPS cells (201B7) are cultured in the culture medium to which both ROCK inhibitor and β-NMN are added in Example 4.

Thereafter, WST assay was performed in the same manner as in Example 1. The results of measuring absorbance values at 450 nm (ref. 595 nm) of each cells cultured in a medium to which both ROCK inhibitor and β-NMN were added are shown in FIG. 4. As shown in FIG. 4, a growth-accelerating effect on iPS cells was obtained in a β-NMN concentration-dependent manner regardless of addition timings of β-NMN.

<Alkali Phosphatase Measurement Test>

First, the iPS cells cultured in the basal medium used in Example 1 were separated from a culture vessel by a cell-peeling solution and recovered. The recovered cells were counted and seeded in each well of a Matrigel-coated 96-well plate at 2000 cells/well. At this time, the ROCK inhibitor and β-NMN having a final concentration of 0 to 1 mM were added to each well. The cells in 96-well plate was cultured at 37° C. for 1 day to allow the cells to adhere, and then the medium containing the ROCK inhibitor was removed from each well, the medium was replaced with a medium obtained by adding, to the basal medium, β-NMN so that a final concentration became 0 to 1 mM, and culturing was performed for 3 to 4 days. During this period, the medium was replaced daily.

Next, after removing the medium in each well, an ethanol-acetone fixation solution was added to fix the cells in each well. After drying the wells, a bicarbonate buffer containing p-nitrophenol triphosphate acid, which is an alkaline phosphatase measurement reagent, was added and incubated at 37° C. for 30 minutes, and then absorbance at 405 nm was measured using a microplate reader.

Figure 5:
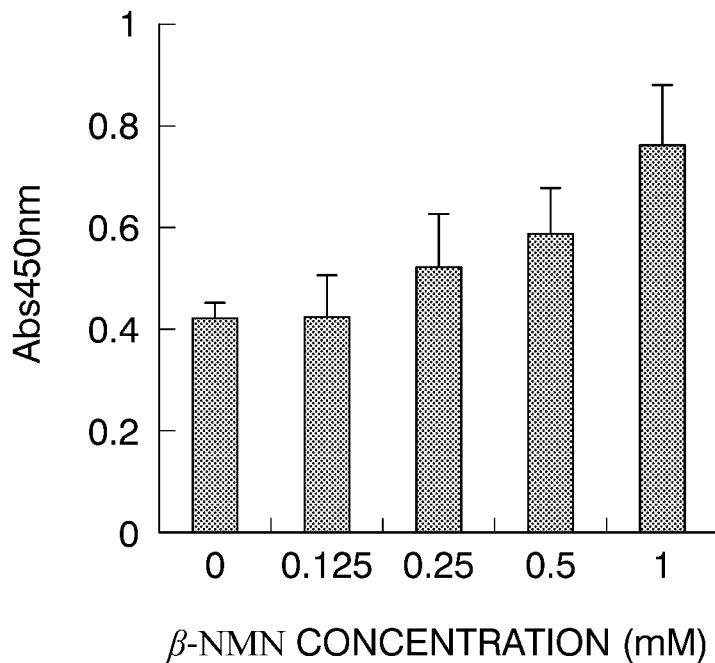
FIG. 5 is a graph showing results of measuring absorbance values at 405 nm for each βNMN concentration of a culture medium by performing an alkaline phosphatase measurement test on wells in which iPS cells (201B7) are cultured in the culture medium to which both ROCK inhibitor and β-NMN are added in Example 4.

The results of the absorbance values at 405 nm of each cells cultured in a medium to which both ROCK inhibitor and β-NMN were added are shown in FIG. 5. As shown in FIG. 5, regardless of addition timings of β-NMN, an absorbance value at 405 nm of the cells cultured in the medium to which β-NMN was added was higher than that of the cells cultured in the β-NMN-free medium. Therefore, iPS cells were confirmed to be able to grow while maintaining undifferentiation properties.

Example 5

Human mesenchymal stem cells (human MSCs) were cultured in a culture medium containing β-NMN, and an effect of β-NMN on proliferative activity was examined.

Human MSCs purchased from Lonza were used. As a basal medium for human MSCs, a dedicated maintenance medium purchased from Lonza was used.

Human MSCs were seeded in 96-well plates (Nunc) at $2 \times 10^3$ cells/well (n=3 to 4). They were cultured at 37° C. in a $CO_2$ incubator to allow them to adhere, and then β-NMN (manufactured by Oriental Yeast Co., Ltd.) was added so that a final concentration became 1.0, 0.1, 0.01, or 0.001 mM, and culture was further performed at 37° C. in a $CO_2$ incubator for 72 hours.

Thereafter, proliferative activity of cells in each well was measured with WST assay. Specifically, after adding a viable cell count reagent SF (Nacalai Tesque) to each well and incubating at 37° C. for 1 to 4 hours, absorbance at 450 nm was measured with the reference wavelength at 620 nm using a microplate reader (absorbance values at 450 nm (ref. 620 nm) (BMG LABTECH). The term "absorbance values at 450 nm (ref. 620 nm)" is an absorbance value at 450 nm using an absorbance value at 620 nm as a reference value, and is specifically a value obtained by subtracting an absorbance value at 620 nm from an absorbance value at 450 nm.

[0045]

The results of the absorbance at 450 nm (ref. 620 nm) in each well for each β-NMN concentration were shown in Table 1. The addition of β-NMN increased the absorbance value and accelerated proliferative activity of human MSCs as well as iPS cells.

TABLE 1

| β-NMN concentration [mM] | Absorbance value at 450 nm (ref. 620 nm) |
| --- | --- |
| 0 (not added) | 0.569 ± 0.0126 |
| 0.001 | 0.573 ± 0.0312 |
| 0.01 | 0.604 ± 0.0587 |
| 0.1 | 0.634 ± 0.0411 |
| 1 | 0.615 ± 0.0340 |

Example 6

The differentiation potential of iPS cells maintained and grown in the presence of β-NMN was confirmed. As iPS cells, a 201B7 line was used.

Specifically, iPS cells were seeded in a 35 mm dish coated with Matrigel (Corning) at $1.5 \times 10^4$ cells/dish. As culture medium in which β-NMN was added to a basal medium (E8 medium) of iPS cells so that a final concentration became 0, 0.25, or 1 mM was used. At the time of seeding, Rho-dependent apoptosis was suppressed using a culture medium to which a Rock inhibitor was added so that a final concentration became 10 μM. The medium was replaced daily and the cells were passaged on day 5 and 6. iPS cells cultured for 5 or more passages in the medium to which β-NMN was added were stained with each of antibodies against SSEA4 and against low sulfated keratan sulfate which are undifferentiated markers, and cells expressing the undifferentiated markers were analyzed with a flow cytometer.

Figure 6:
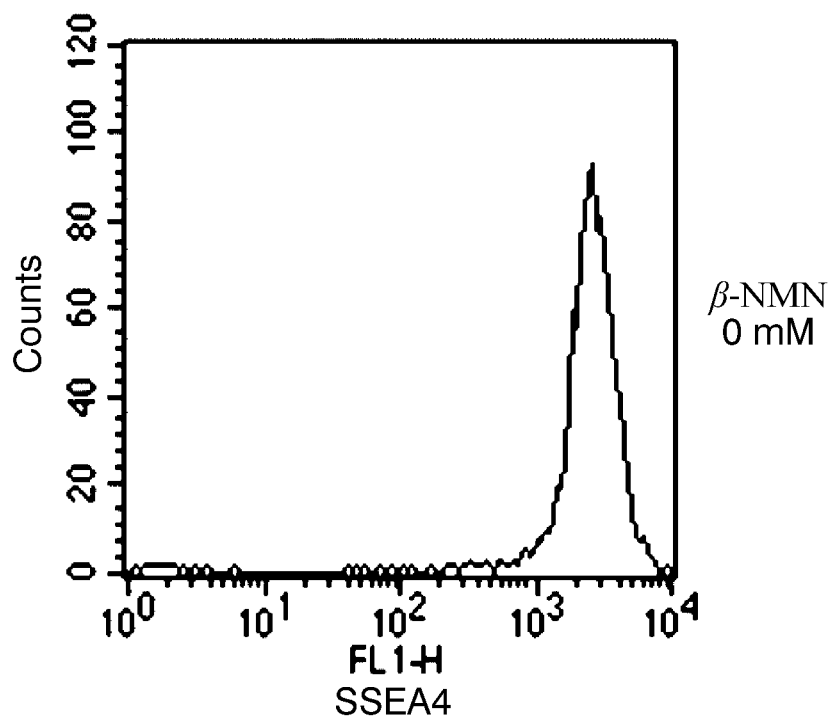
FIG. 6 is a graph showing results of flow cytometry of iPS cells (201B7) which are stained with an anti-SSEA4 antibody after being cultured in a β-NMN-free culture medium in Example 6.
Figure 7:
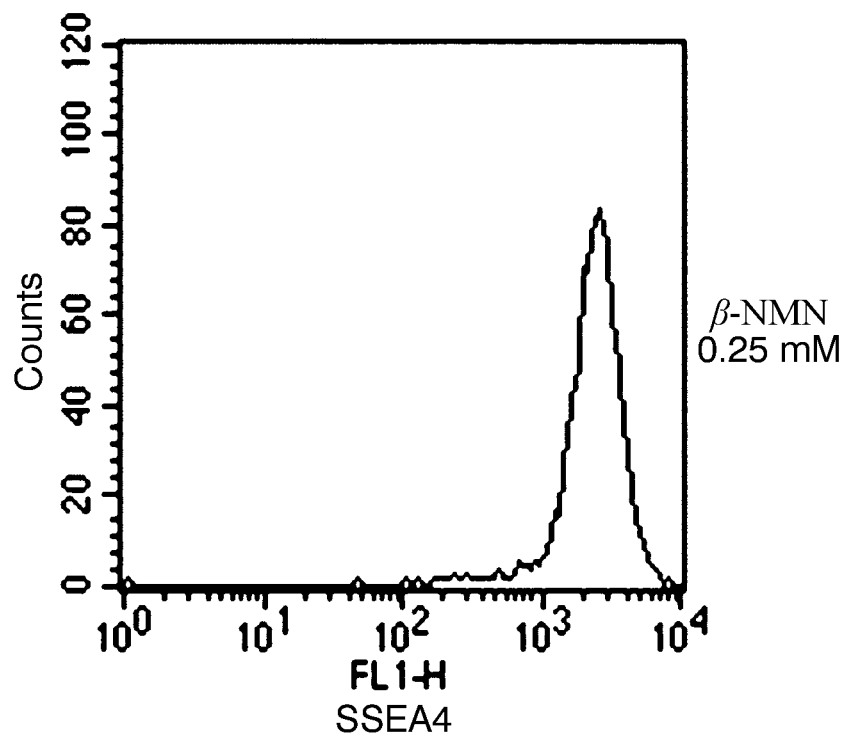
FIG. 7 is a graph showing results of flow cytometry of iPS cells (201B7) which are stained with an anti-SSEA4 antibody after being cultured in a culture medium containing 0.25 mM of β-NMN in Example 6.
Figure 8:
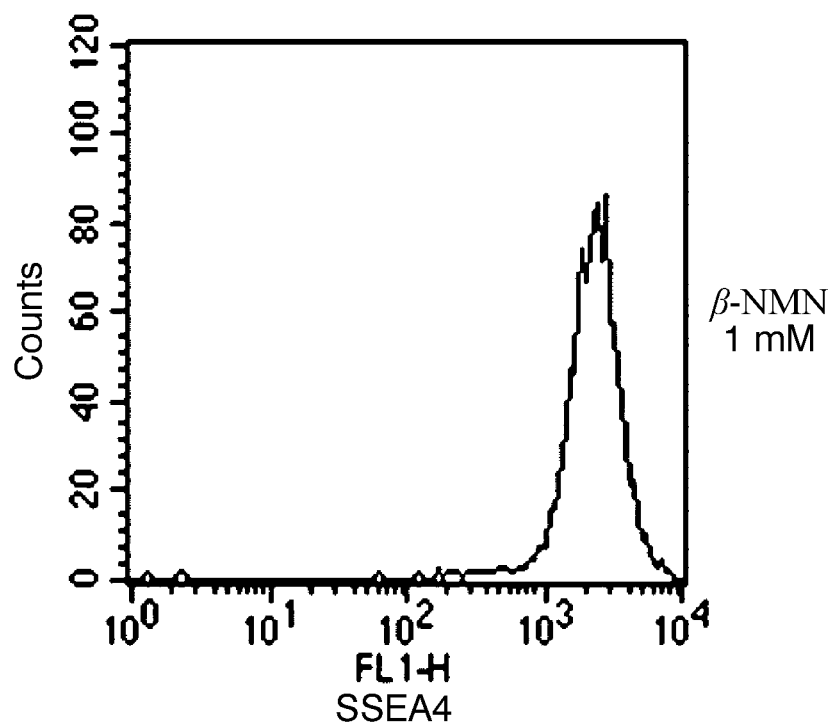
FIG. 8 is a graph showing results of flow cytometry of iPS cells (201B7) which are stained with an anti-SSEA4 antibody after being cultured in a culture medium containing 1 mM of β-NMN in Example 6.
Figure 9:
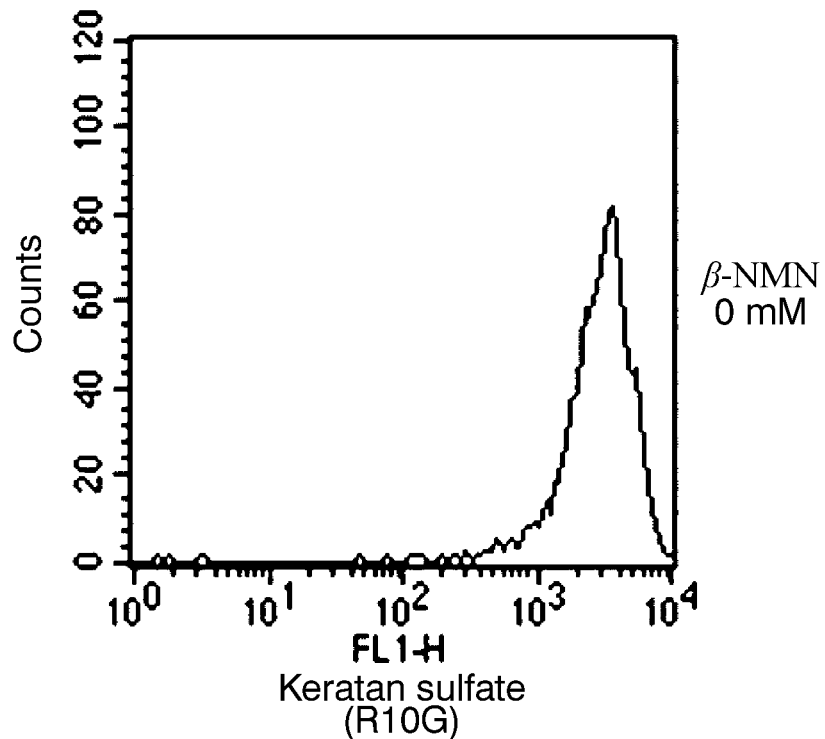
FIG. 9 is a graph showing results of flow cytometry of iPS cells (201B7) which are stained with an anti-low sulfated keratan sulfate antibody (R10G) after being cultured in a β-NMN-free culture medium in Example 6.
Figure 10:
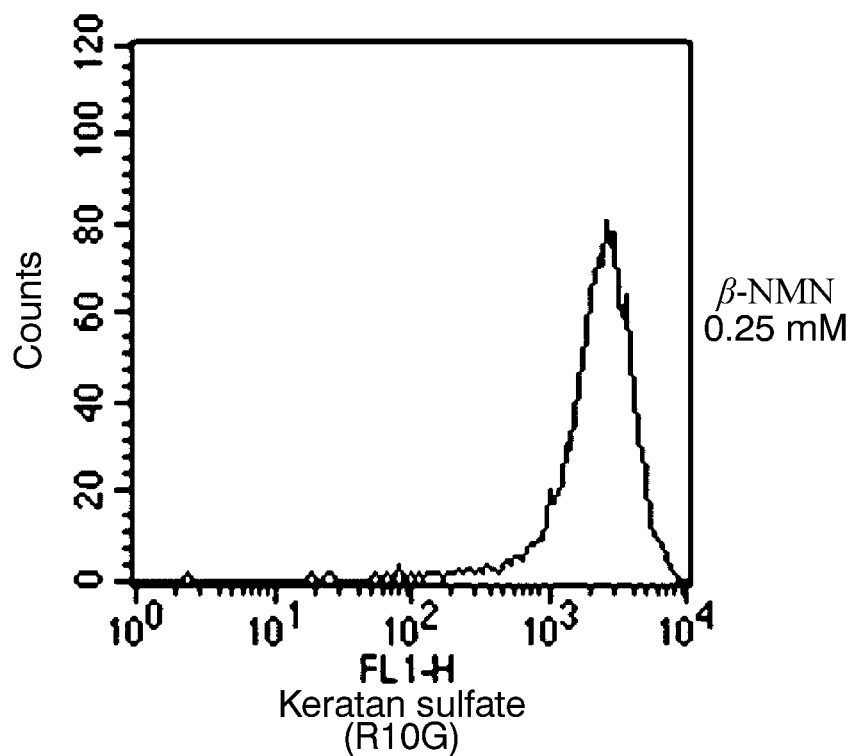
FIG. 10 is a graph showing results of flow cytometry of iPS cells (201B7) which are stained with an anti-low sulfated keratan sulfate antibody (R10G) after being cultured in a culture medium containing 0.25 mM of β-NMN in Example 6.
Figure 11:
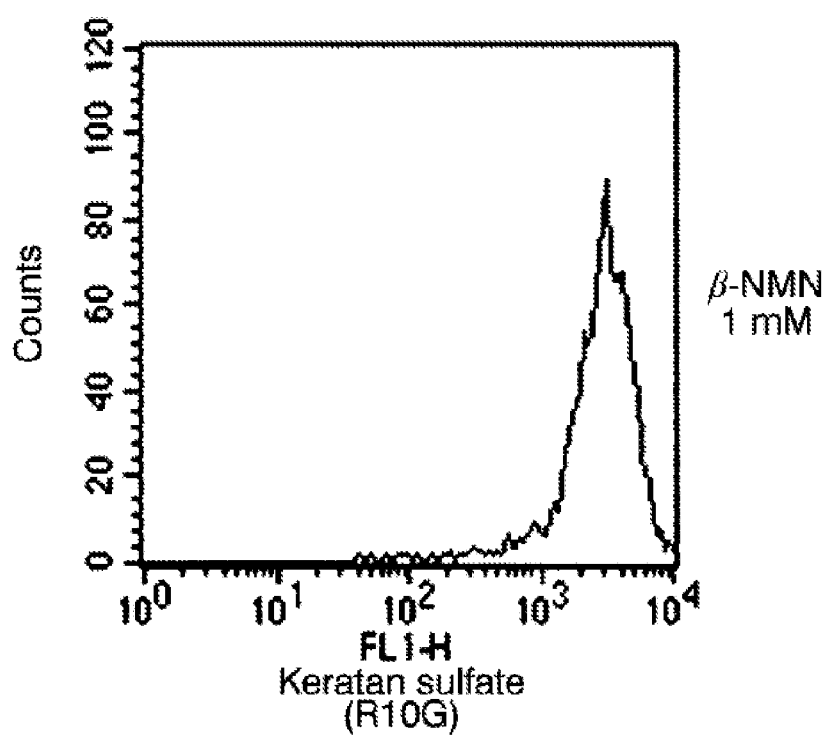
FIG. 11 is a graph showing results of flow cytometry of iPS cells (201B7) which are stained with an anti-low sulfated keratan sulfate antibody (R10G) after being cultured in a culture medium containing 1 mM of β-NMN in Example 6.

FIGS. 6 to 8 are graphs each showing results of flow cytometry of iPS cells stained with an anti-SSEA4 antibody after being cultured at β-NMN concentrations of 0, 0.25, and 1 mM, respectively. FIGS. 9 to 11 are graphs each showing results of flow cytometry of iPS cells stained with an anti-low sulfated keratan sulfate antibody (R10G) after being cultured at β-NMN concentrations of 0, 0.25, and 1 mM, respectively. Expression of SSEA4 and low sulfated keratan sulfate was maintained in the iPS cells cultured in the presence of 0.25 mM or 1 mM of β-NMN as in the iPS cells cultured in the absence of β-NMN (0 mM of β-NMN concentration). Based on these results, it was confirmed that cell growth can be accelerated while maintaining differentiation potential by culturing iPS cells in the presence of β-NMN.

The invention claimed is:

1. A method for accelerating growth of a mesenchymal stem cell, comprising:
   culturing the mesenchymal stem cell in a maintenance culture medium that comprises a β-nicotinamide mononucleotide, or a pharmaceutically acceptable salt thereof, or a solvate thereof, wherein
   a concentration of the β-nicotinamide mononucleotide of the maintenance culture medium is in a range from 0.05 to 2.0 mM, and
   mesenchymal stem cell growth occurs while maintaining multipotency thereof.

2. The method for accelerating growth of a mesenchymal stem cell according to claim 1, wherein the concentration of the β-nicotinamide mononucleotide of the maintenance culture medium is in a range from 0.05 to 1.0 mM.

3. The method for accelerating growth of a mesenchymal stem cell according to claim 1, wherein the concentration of the β-nicotinamide mononucleotide of the maintenance culture medium is in a range from 0.1 to 2.0 mM.

4. The method for accelerating growth of a mesenchymal stem cell according to claim 3, wherein the concentration of the β-nicotinamide mononucleotide of the maintenance culture medium is in a range from 0.1 to 1.0 mM.

5. A method for culturing a pluripotent stem cell, comprising:
    culturing the pluripotent stem cell in a maintenance culture medium that comprises a β-nicotinamide mononucleotide, or a pharmaceutically acceptable salt thereof, or a solvate thereof, wherein
    a concentration of the β-nicotinamide mononucleotide of the maintenance culture medium is in a range from 0.1 to 2.0 mM,
    the pluripotent stem cell is at least one cell selected from the group consisting of an embryonic stem cell and an induced pluripotent stem cell, and
    pluripotent stem cell growth occurs while maintaining pluripotency thereof.

6. The method for culturing a pluripotent stem cell according to claim 5, wherein the concentration of the β-nicotinamide mononucleotide of the maintenance culture medium is in a range from 0.1 to 1.0 mM.

7. The method for culturing a pluripotent stem cell according to claim 5, wherein the concentration of the β-nicotinamide mononucleotide of the maintenance culture medium is in a range from 0.2 to 0.8 mM.

* * * * *